United States Patent [19]
Brock et al.

[11] Patent Number: 5,482,636
[45] Date of Patent: Jan. 9, 1996

[54] PROCESS FOR THE QUATERNIZATION OF TRIETHANOLAMINE FATTY ACID ESTERS AND IMIDAZOLINAMIDES AND THE USE OF THE REACTION MIXTURES IN LAUNDRY SOFTENER COMPOSITIONS

[75] Inventors: Michael Brock, Schermbeck; Peter Hardt, Monheim; Helmut Klimmek; Dolf Stockhausen, both of Krefeld, all of Germany

[73] Assignee: Huels Aktiengesellschaft, Marl, Germany

[21] Appl. No.: 283,511

[22] Filed: Aug. 1, 1994

Related U.S. Application Data

[62] Division of Ser. No. 172,276, Dec. 23, 1993.

[30] Foreign Application Priority Data

Dec. 23, 1992 [DE] Germany ............... 42 43 862.4

[51] Int. Cl.$^6$ .............. D06M 13/322; D06M 13/46; C07D 233/00; C07C 229/00
[52] U.S. Cl. .............. 252/8.8; 252/8.6; 106/243; 106/244; 548/334.1; 562/571; 554/110
[58] Field of Search .............. 252/8.8, 8.6; 106/243, 106/244; 548/334.1; 562/571; 554/110

[56] References Cited

U.S. PATENT DOCUMENTS

| | | | |
|---|---|---|---|
| 3,915,867 | 10/1975 | Kang et al. | 252/8.8 |
| 4,233,451 | 11/1980 | Pracht et al. | 548/316.4 |
| 4,429,859 | 2/1984 | Steiner et al. | 252/8.8 |
| 4,720,383 | 1/1988 | Drach et al. | 548/313.7 |
| 4,830,771 | 5/1989 | Ruback et al. | 252/8.8 |
| 4,865,614 | 9/1989 | Ploog et al. | 252/8.8 |
| 4,954,635 | 9/1990 | Rosario-Jansen et al. | 548/352.1 |
| 5,013,846 | 5/1991 | Walley | 548/338.1 |
| 5,116,520 | 5/1992 | Lichtenwalter et al. | 252/8.6 |
| 5,296,622 | 3/1994 | Uphues et al. | 554/103 |

FOREIGN PATENT DOCUMENTS

| | | |
|---|---|---|
| 3710064 | 10/1988 | Germany . |
| 4215689 | 11/1993 | Germany . |

*Primary Examiner*—Anthony Green
*Attorney, Agent, or Firm*—Oblon, Spivak, McClelland, Maier, & Neustadt

[57] ABSTRACT

A process for the quaternization of triethanolamine fatty acid esters and imidazolinamides with customary quaternizing agents in a reaction medium containing alkoxylated naturally occurring fats or oils, or mixtures thereof with free fatty acids, monoglycerides and/or diglycerides in the substantial absence of 2-propanol, and the use of the resulting reaction mixtures as the active components in laundry softener compositions.

4 Claims, No Drawings

PROCESS FOR THE QUATERNIZATION OF TRIETHANOLAMINE FATTY ACID ESTERS AND IMIDAZOLINAMIDES AND THE USE OF THE REACTION MIXTURES IN LAUNDRY SOFTENER COMPOSITIONS

This is a division of application Ser. No. 08/172,276, filed on Dec. 23, 1993.

BACKGROUND OF THE INVENTION

1. Field of the Invention

The present invention relates to a process for the quaternization of triethanolamine fatty acid esters and imidazolinamides in a reaction medium containing alkoxylated fats or oils and to the use of the resulting reaction mixtures as the active ingredients in laundry softener compositions.

2. Discussion of the Background

Quaternized fatty acid esters of triethanolamine (N-alkyl-N,N,N-trihydroxyethylammonium fatty acid ester salts, called ester-quat below) or quaternized imidazolinamides (1-alkyl-2-alkyl-3-alkylamidoimidazolinium salts, called imidazolinium-quat below) have previously been used as the active ingredients in laundry softener compositions. More detailed descriptions both of the preparation and of the use of ester- and imidazolinium-quats (called generally quats below) as laundry softener active ingredients can be found in EP 0 295 385, DE 37 10 064, WO 91/17974, US 3 915 867, BE 888 678, DD 159 263 and EP 0 431 652.

The quaternizing agents conventionally used are, for example, benzyl halides, methyl halides, dimethyl sulphate or dipropyl sulphate. The quaternization reaction is conventionally carried out in a low molecular weight alcohol, such as 2-propanol, as solvent. The 2-propanol is not removed after quaternization, so that the quats are marketed as 85–90% strength compositions. The 2-propanol is used to ensure a flowable consistency, both of the reaction mixtures and of the quats formed, at the quaternization temperature (40–95° C.). This is of importance for technical production reasons. Furthermore, the flowable consistency thus obtained assists in successful conversion of the quats to laundry softener formulations. The 2-propanol employed functions exclusively as a diluent and has no additional softening influence by interaction with the quats. However, the use of 2-propanol presents problems, due to its low flash point (12° C.).

DE-A 42 15 689 describes the use of alkoxylated fats as the sole active ingredient in laundry softener compositions or in mixtures with the conventional nitrogen-containing cationic active softening ingredients, such as N,N-distearyl-N,N-dimethylammonium salts, quaternized or protonated imidazoline derivatives, quaternized fatty acid esters of triethanolamine and 2,3-dihydroxypropyl-trimethylammonium salt derivatives. These quaternized compounds are provided by quaternization according to conventional procedures in 2-propanol as solvent, and subsequent combining of the quaternized compounds with the alkoxylated fats. When mixtures of these alkoxylated fats with nitrogen-containing cationic active ingredients, such as ester-quats and imidazolinium-quats, are used, the mixtures are employed as 90% concentrates in 2-propanol.

SUMMARY OF THE INVENTION

Accordingly, one object of the present invention is to provide a reaction medium and process employing the medium for the preparation of quaternized triethanolamine fatty acid esters and imidazolinamides which provide a synergistic softening effect with respect to the use of quats alone, while maintaining a high flowability of the reaction mixture.

Another object of the present invention is to provide a reaction medium and process employing the medium for the preparation of quats which provides improved softening compared to the same amount of quats in 2-propanol.

Another object of the present invention is to provide a reaction medium used in a method for preparing quats which results in a product having a flash point $\geq 100°$ C.

Another object of the present invention is to provide a laundry softener composition containing the above-mentioned combination of quats and the alkoxylated fat or oil reaction medium in the absence of 2-propanol.

These and other objects of the present invention which will become evident from the following detailed description, have been satisfied by the discovery of a process for the quaternization of triethanolamine fatty acid esters or imidazolinamides comprising:

contacting the triethanolamine fatty acid ester or imidazolinamide with a quaternization agent in a reaction medium comprising alkoxylated naturally occurring fats or oils, or mixtures thereof with free fatty acids, monoglycerides, diglycerides or a combination thereof, wherein the reaction medium and resulting quaternized product mixture are substantially free of 2-propanol.

DESCRIPTION OF THE PREFERRED EMBODIMENTS

The present invention relates to a process for the quaternization of triethanolamine fatty acid esters and imidazolinamides with customary quaternizing agents, characterized in that alkoxylated naturally occurring fats or oils or mixtures thereof with free fatty acids, monoglycerides and/or diglycerides are employed as the reaction medium, in the substantial absence of 2-propanol. In the present invention, the phrases "substantial absence of 2-propanol" and "substantially free of 2-propanol" mean that in the reaction mixtures obtained by the process of the present invention, the amount of 2-propanol present is less than 1%, preferably less than 0.1%.

The triethanolamine fatty acid esters used in the present invention are prepared by esterification of triethanolamine with fatty acids or fatty acids methyl esters having from 10 to 40 carbons, preferably 10 to 20 carbons. The fatty acids or fatty acids methyl esters may be used singly or in combination in the esterification reaction. Since many fatty acids or fatty acids methyl esters are commercially available as mixtures of $C_{10}$–$C_{20}$ fatty acids or fatty acids methyl esters, such mixtures may be used in the preparation of the triethanolamine fatty acid esters.

The imidazolinamides used in the present invention are 1-alkyl-2-alkyl-3-hydrocarbylamidoimidazolines wherein the substituents in the 1 and 2 positions are linear, branched or cyclic alkyl having from 1 to 20 carbon atoms. The hydrocarbyl group on the 3-hydrocarbylamido substituent is a hydrocarbon group derived from fatty acids having from 10 to 40 carbon atoms, preferably 10 to 20 carbon atoms. The hydrocarbylamido substituent may be prepared by amidating the nitrogen in the 3-position of the imidazoline ring with one or more fatty acids, including the saturated fatty acids and the unsaturated fatty acids, preferably the singly unsaturated fatty acids. As in the case of the triethanolamine fatty acid esters of the present invention, commercial mixtures of fatty acids or fatty acid methyl esters, such as those having from 10 to 20 carbon atoms may be used.

The fats or oils include the triglycerides and mixtures thereof with free fatty acids, monoglycerides and/or diglycerides. The alkoxylation reaction can be carried out by conventional methods, such as those disclosed in DE-A 36 17 657 and DE-A 38 26 179.

The alkoxylated fats or oils are prepared by alkoxylating the fats or oils with one or more epoxides, such as ethylene oxide, propylene oxide or butylene oxide. If more than one epoxide is used, these can be reacted with the fats either in succession or simultaneously. The epoxide is used in an amount of 5 to 30 wt % of the epoxide based on the amount of the oil or fat, preferably 10 to 20% of the epoxide.

Before the quaternization reaction, the triethanolamine fatty acid esters or imidazolinamides and the alkoxylated fats are combined in a ratio of 1:99 to 90:10, preferably 5:95 to 80:20. The quaternization is carried out under conventional temperature and pressure conditions using customary quaternizing agents, such as benzyl halides, methyl halides, dimethyl sulphate and dipropyl sulphate. Dimethyl sulphate is preferably used.

The resulting reaction mixtures of the quaternized triethanolamine fatty acid esters or imidazolinamides and the alkoxylated naturally occurring fats or oils or mixtures thereof with free fatty acids, monoglycerides and/or diglycerides are useful as active ingredients in laundry softener compositions. The content of the reaction mixture of the present invention in the laundry softener composition is 1 to 50% by weight, preferably 5–30% by weight, with the remainder of the composition comprising customary additives, such as electrolytes, emulsifiers, dispersing agents, fragrances, dyestuffs and a suitable conventional laundry softener carrier such as water.

By replacing the conventional combination of quats in 2-propanol by the quats in alkoxylated fats or oils of the present invention, the amount of quats can be reduced by up to 68% with the same softening action. The alkoxylated fats employed all have flash points above 100° C. Additionally, the product mixture provided by the process of the present invention has a flash point of $\geq 100°$ C.

Having generally described this invention, a further understanding can be obtained by reference to certain specific examples which are provided herein for purposes of illustration only and are not intended to be limiting unless otherwise specified.

Examples

Preparation of Quats in Alkoxylated Fats

The batches described in Examples 1–4 are pale-colored pasty substances which have a melting range of 20–50° C.

Example 1: Preparation of ester-quats in propoxylated palm oil

Triethanolamine fatty acid ester (degree of esterification: 1.5, C chain distribution of the fatty acid on which it is based: 3% by weight of $C_{14}$, 38% by weight of $C_{16}$, 3% by weight of $C_{16}$-ene, 9% by weight of $C_{18}$ and 47% by weight of $C_{18}$-ene) and the reaction product from the reaction of palm oil with 15% by weight of propylene oxide ("propoxylated palm oil") were initially introduced into a 250 ml three-necked flask fitted with an intensive cooler, dropping funnel and contact thermometer. After flushing the apparatus with nitrogen, the mixture was heated to 60° C. and dimethyl sulphate was added dropwise over the course of 15 minutes, while stirring continuously. The temperature of the mixture rose temporarily to 90–95° C. After the mixture had been stirred at 60° C. for 10 hours, no further dimethyl sulphate was detected (detection with the aid of Draeger tubes from Draeger, lower detection limit 0.005 ppm).

|  | BATCH | | |
| --- | --- | --- | --- |
|  | A | B | C |
| Amount of triethanolamine fatty acid ester employed [g] | 100 | 100 | 45 |
| Amount of propoxylated employed [g] | 11.1 | 17.7 | 105.0 |
| Weight ratio of triethaolamine fatty acid ester to propoxylated palm oil | 90:10 | 85:15 | 30:70 |
| Amount of dimethyl sulfate employed [g] | 21.3 | 21.3 | 9.6 |

Example 2: Preparation of ester-quats in propoxylated skin fat

The experimental procedure was analogous to that described in Example 1, with the difference that the reaction product from the reaction of skin fat with 15% by weight of propylene oxide ("propoxylated skin fat") was employed in this example instead of the propoxylated palm oil.

|  | BATCH | | |
| --- | --- | --- | --- |
|  | D | E | F |
| Amount of triethanolamine fatty acid ester employed [g] | 100 | 100 | 45 |
| Amount of propoxylated palm oil employed [g] | 11.1 | 17.7 | 105.0 |
| Weight ratio of triethanolamine fatty acid ester to propoxylated palm oil | 90:10 | 85:15 | 30:70 |
| Amount of dimethyl sulfate employed [g] | 21.3 | 21.3 | 9.6 |

Example 3: Preparation of imidazolinium-quats in propoxylated palm oil

The experimental procedure was analogous to that described in Example 1.

2-Alkyl-3-hydrocarbylamidoethylimidazoline (C chain distribution of the fatty acid on which the 3-hydrocarbyl substituent is based: 3% by weight of $C_{14}$, 38% by weight of $C_{16}$, 3% by weight of $C_{16}$-ene, 9% by weight of $C_{18}$, 47% by weight of $C_{18}$-ene) and the reaction product from the reaction of palm oil and 15% by weight of propylene oxide ("propoxylated palm oil") were initially introduced into the reaction vessel. After flushing the apparatus with nitrogen, the mixture was heated to 60° C. and dimethyl sulphate was added dropwise over the course of 15 minutes, while stirring continuously. The reaction temperature rose temporarily to 90–95° C. After the mixture had been stirred at 60° C. for 10 hours, no further dimethyl sulphate was detected (for the detection, see Example 1).

|  | BATCH | | |
| --- | --- | --- | --- |
|  | G | H | K |
| Amount of imidazolinamide fatty acid ester employed [g] | 135.0 | 127.5 | 45.0 |
| Amount of propoxylated palm oil employed [g] | 15.0 | 22.5 | 105.0 |
| Weight ratio of imidazolinamide fatty acid ester to propoxylated palm oil | 90:10 | 85:15 | 30:70 |
| Amount of dimethyl sulfate employed [g] | 24.9 | 23.4 | 8.3 |

Example 4: Preparation of imidazolinium-quats in propoxylated skin fat

The experimental procedure was analogous to that described in Example 3, with the difference that the reaction product from the reaction of skin fat with 15% by weight of propylene oxide ("propoxylated skin fat") was employed in this example instead of propoxylated palm oil.

|  | BATCH | | |
| --- | --- | --- | --- |
|  | L | M | N |
| Amount of imidazolinamide fatty acid ester employed [g] | 135.0 | 127.5 | 45.0 |
| Amount of propoxylated palm oil employed [g] | 15.0 | 22.5 | 105.0 |
| Weight ratio of imidazolinamide fatty acid ester to propoxylated palm oil | 90:10 | 85:15 | 30:70 |
| Amount of dimethyl sulfate employed [g] | 24.9 | 23.4 | 8.3 |

Description of the Test Method for the Softening Action

The softening action of batches A to N from Examples 1 to 4 was determined as follows: a load of 72 terry hand towels (44 cm×30 cm, about 60 g, from WFK-Testgewebe GmbH) were washed once in a machine at 95° C., even if all 72 towels were not used (for reasons of uniform wear and tear), with 100 g of a commercially available heavy-duty detergent (PERSIL, Henkel), rinsed and spun. This was followed by a wash at 95° C. without detergent, including brief spinning, to provide clean, damp towels containing about 2.5 times their dry weight of water which were ready for manual softening.

In accordance with the test plan as described in Table A, in each case 9 towels were softened in 9 rinsing liquors containing the standard (=S, MARLOSOFT E 90 [1] for test batches A to F and MARLOSOFT IQ 90 [2] for test batches G to N) and 9 towels were softened in 9 rinsing liquors containing the test substance (=T, batches A to N). In each case, 2 liters of tap water (12° dH) as rinsing liquor containing 0.35 g of S (calculated as active substance) per liter of rinsing liquor, or an amount of test substance T to be chosen as desired, were predispersed in plastic bowls and the damp towels were left in the mixture for 10 minutes. After 5 minutes, the towels were turned once. The softened towels were spun individually for 30 seconds each and dried in static air on a clothes-horse.

1) MARLOSOFT E 90: ester-quat, 90% strength in 2-propanol, Huls

2) MARLOSOFT IQ 90: imidazolinium-quat, 90% strength in 2-propanol, Huls

TABLE A

Test plan for soft handle testing with 6 testers
Tester Towel combination with coded identification

| 1 | SST |
| 2 | SST |
| 3 | SST |
| 4 | STT |
| 5 | STT |
| 6 | STT |

S = Comparison substance (standard), T = Invention (Test substance)

In each case 3 towels in coded form were presented to the 6 testers in accordance with Table A. The task for the tester was to discover, by sensory assessment, the towel which was treated differently. If this was possible, the tester noted whether the towel treated differently felt softer or rougher. The overall result was expressed with the aid of a points scale from −6 to +6. For example, if tester 1 discovered the towel treated differently with T and found it to be softer than the other two towels, 1 plus point was scored. If he finds it to be rougher, 1 minus point was scored. If the tester could detect no difference between the 3 towels, 0 points were scored. If tester 1 was of the opinion that a towel treated with S differed from the others, 0.5 plus point was scored if the tester evaluated this as being rougher, and 0.5 minus points if the tester evaluated it as being softer. The procedure was analogous for the other testers. The points were then totalled. If the points total was 0, there was no difference in soft handle between the towels treated with S and those treated with T. If the points total was greater than 0, the handle of the towels treated with T was softer than that of the towels treated with S. If the points total was less than 0, the situation was the reverse.

Example 5: Testing of the softening of the batches A to F described in Examples 1 and 2 (standard: MARLOSOFT E 90)

In a series of experiments, terry hand towels were softened in rinsing liquors which comprise various concentrations of batches A to F described in Examples 1 and 2. The rinsing liquor concentration was varied until the treated towels were evaluated as just as soft as the towels treated with MARLOSOFT E 90. As the result of the handle testing, the total of all the points must thus be 0. The following table shows the concentrations of batches A to F needed to obtain the same soft handle effected by 0.35 g of MARLOSOFT E 90 (calculated on the active content) per liter of rinsing liquor.

| Batch | Total Concentration of the batch [g/l] | Ester-quat content [g/l] | Saving in ester- quat in comparison with the standard (%) |
| --- | --- | --- | --- |
| A | 0.33 | 0.30 | 14 |
| B | 0.30 | 0.27 | 23 |
| C | 0.46 | 0.14 | 60 |
| D | 0.31 | 0.28 | 20 |
| E | 0.28 | 0.24 | 31 |
| F | 0.60 | 0.18 | 48 |

It was found impressively that the content of ester-quat required could be reduced with all the batches, sometimes drastically. The amount of ester-quat saved was up to 60%. For batches A, B, D and E, additionally, even the total concentration of the batches employed, taking into consideration the amount of propoxylated palm oil or skin fat, was lower than the amount of standard ester-quat employed of 0.35 g per liter of rinsing liquor.

Example 6: Testing of the softening of batches G to N described in Examples 3 and 4 (standard: SOFT IQ 90 )

The procedure followed was analogous to that described in Example 5. Instead of the standard MARLOSOFT E 90, the standard MARLOSOFT IQ 90 was used.

| Batch | Total Concentration of the batch [g/l] | Imidazo- linium- quat con- tent [g/l] | Saving in imidazolinium- quat comparison with the standard [%] |
| --- | --- | --- | --- |
| G | 0.27 | 0.24 | 31 |
| H | 0.29 | 0.25 | 28 |
| K | 0.37 | 0.11 | 68 |
| L | 0.30 | 0.27 | 22 |
| M | 0.28 | 0.24 | 31 |
| N | 0.40 | 0.12 | 65 |

As in Example 5, here also it was found that the content of imidazolinium-quat required could be reduced by up to 68% with addition of propoxylated palm oil or skin fat, with the same softening effect.

For batches G, H, L and M, additionally, even the total concentration of the batches employed, taking into consideration the amount of propoxylated palm oil or skin fat, was lower than the standard imidazolinium-quat content employed of 0.35 g per liter of rinsing liquor.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A quaternized triethanolamine fatty acid ester or imidazolinamide composition prepared by contacting a triethanolamine fatty acid ester or imidazolinamide with a quaternization agent in a reaction medium comprising alkoxylated naturally occurring fats or oils, or mixtures thereof wherein the reaction medium and resulting quaternized composition are substantially free of 2-propanol, such that the resulting quaternized composition has a flash point of $\geq 100°$ C.

2. A laundry softener composition comprising an effective laundry softening amount of a reaction mixture obtained by contacting a triethanolamine fatty acid ester or imidazolinamide with a quaternization agent in a reaction medium comprising alkoxylated naturally occurring fats or oils, or mixtures thereof, wherein the reaction medium and resulting quaternized product mixture are substantially free of 2-propanol; and a suitable carrier.

3. The laundry softener composition according to claim 2, wherein said reaction mixture is present in the laundry softener composition in an amount of from 1 to 50%.

4. The laundry softener composition according to claim 2, wherein said reaction mixture is present in the laundry softener composition in an amount of from 5–30%.

* * * * *